US 8,067,203 B2

(12) United States Patent
Chien et al.

(10) Patent No.: US 8,067,203 B2
(45) Date of Patent: Nov. 29, 2011

(54) COMPOSITION FOR TREATING PORCINE PROGRESSIVE ATROPHIC RHINITIS AND MAKING PROCESS THEREOF

(75) Inventors: Maw-Sheng Chien, Taichung (TW); Cheng-I Liu, Taichung (TW); Chih-Ming Liao, Yun-Lin County (TW)

(73) Assignee: National Chung-Hsing University, Taichung (TW)

( * ) Notice: Subject to any disclaimer, the term of this patent is extended or adjusted under 35 U.S.C. 154(b) by 51 days.

(21) Appl. No.: 12/286,372

(22) Filed: Sep. 30, 2008

(65) Prior Publication Data

US 2009/0226965 A1   Sep. 10, 2009

Related U.S. Application Data

(62) Division of application No. 11/206,071, filed on Aug. 18, 2005, now abandoned.

(30) Foreign Application Priority Data

Aug. 20, 2004  (TW) .............................. 93125156 A

(51) Int. Cl.
*C12N 15/09* (2006.01)
*A61K 39/102* (2006.01)
*A61K 39/00* (2006.01)
*A61K 45/00* (2006.01)

(52) U.S. Cl. ................. 435/69.3; 424/255.1; 424/278.1; 424/184.1

(58) Field of Classification Search ........................ None
See application file for complete search history.

(56) References Cited

U.S. PATENT DOCUMENTS 5,885,589 A * 3/1999 Foged et al. ............... 424/255.1
6,057,122 A * 5/2000 Davidson ..................... 435/68.1

FOREIGN PATENT DOCUMENTS

EP            1657248 A2 *  5/2006

OTHER PUBLICATIONS

Gram et al., Expression of cDNA using a pER32a expression vector in the Novagen BL21 (DE3) pLYSS system, BIOL 4774; 2004.*

* cited by examiner

*Primary Examiner* — Vanessa L Ford
*Assistant Examiner* — Lakia Tongue
(74) *Attorney, Agent, or Firm* — Charles E. Baxley

(57) ABSTRACT

The present invention relates to an animal vaccine directed to progressive atrophic rhinitis (PAR), comprising at least two fragments of recombinant subunit *Pasteurella multocida* toxins (rsPMT) capable of eliciting the production of antibodies against *Pasteurella multocida* associated with PAR, and to a method for producing the animal vaccine of the invention, said fragments each having an amino acid sequence that substantially corresponds to the 2-486, 486-986 or 986-1281 amino acid residues of *Pasteurella multocida* toxin (PMT), respectively. Also disclosed is a multivalent animal vaccine, comprising said fragments as active components against PAR, and at least a pathogenic antigen or epitope thereof associated with other animal disease(s), such as inactivated gE-deleted Pseudorabies virus.

3 Claims, 9 Drawing Sheets

A

B

C

D

COMPOSITION FOR TREATING PORCINE PROGRESSIVE ATROPHIC RHINITIS AND MAKING PROCESS THEREOF

CROSS REFERENCE

The present application is Division of U.S. application Ser. No. 11/206,071 by the same inventors filed on 18 Aug., 2005 now abandoned.

BACKGROUND OF THE INVENTION

1. Field of the Invention

This invention is generally in the field of veterinary vaccines, vaccine compositions, and methods of producing the same. Particularly, provided herein are the vaccines for immunizing animal against progressive atrophic rhinitis (PAR), which comprise a combination of at least two fragments of recombinant subunit *Pasteurella multocida* toxins (rsPMT) each having an amino acid sequence that substantially corresponds to the 2-486, 486-986 or 986-1281 amino acid residues of *Pasteurella multocida* toxin (PMT).

2. Description of Related Art

Progressive atrophic rhinitis (PAR) is an important upper respiratory disease in swine. The characteristic lesions include turbinate bone hypoplasia, facial distortion and nasal hemorrhage as a result of frequent sneezing. Moreover, PAR causes significant global economic loss in swine production due to growth retardation. Several studies have demonstrated that *Pasteurella multocida* toxin (PMT) is the major virulence factor responsible for the turbinate atrophy seen in PAR (see, for example, Ackermann M R et al. 1996; Am J Vet Res 57(6):848-852; and Lax A J & Chanter N. 1990; J Gen Microbiol 136:81-87). Inoculation of PMT alone could reproduce all major symptoms of PAR in experimentally challenged pigs. Either aerosolized or injected into swine, PMT causes severe turbinate atrophy and reduces weight gain (Kamp E M & Kimman T G 1988; Am. J. Vet. Res. 49:1844-1849). The mechanisms by which PMT reduces weight gain and conchal bone atrophy have been widely studied. Results of several studies indicate that PMT could increase bone resorption and reduce bone formation by altering the functions of osteoblasts and osteoclasts.

The molecular basis for the virulence of PMT remains unclear, but may be associated with the activation of osteoclasts or inactivation of osteoblasts. It has been demonstrated that PMT is a potent mitogen for several types of cells such as Swiss 3T3 fibroblasts. PMT was able to induce half-maximal stimulation of DNA synthesis and cell proliferation at doses as low as 1 pM. The effect of PMT on porcine osteoclasts and osteoblasts has been investigated using an in vitro cell culture system. Exposure of bone marrow cells to Vitamin D3 and PMT during growth led to an increase in cell numbers and earlier appearance of osteoclasts compared to controls. Low concentrations of PMT resulted in growth retardation and decreased nodule formation in osteoblasts, while high concentrations of PMT increased cell death and inhibited nodule formation (Gwaltney S M et al. 1997; Vet Pathol 34(5):421-430). PMT also stimulates cell proliferation, but impairs cell maturation and cell function in primary cultures of rat osteoblasts. These findings suggest that PMT may increase bone resorption and decrease bone apposition, eventually leading to progressive osteolysis and continuous bone atrophy.

Many potential bacterial pathogens can colonize the nasal cavity or tonsils of swine and *P. multocida* is one of the primary opportunistic pathogens able to cause porcine respiratory disease complex (PRDC). In fact, PAR is considered a contagious respiratory disease with high prevalence throughout the areas of the world where modern pig husbandry is practiced. Antibiotics, vaccination and good management can reduce the severity and frequency of PAR. However, overuse of antibiotics is a source of public health concern and vaccination has emerged as the most attractive approach in controlling PAR (Foged N T et al. Vet Rec 1989; 125(1):7-11; Kobisch M, Pennings A, Vet Rec 1989; 124(3):57-61; and Sakano T et al. J Vet Med Sci 1997; 59(1):55-57).

The entire PMT gene (toxA) encoding a protein of 1285 amino acids has been cloned and expressed in *E. coli* (Petersen S K & Foged N T 1989; Infect Immun 57(12):3907-3913). A recombinant PMT derivative lacking N-terminal amino acid residues 27-147 was shown to induce a protective response against challenge with a lethal dose of PMT in mice (Petersen S K et al. 1991; Infect Immun 59(4):1387-1393), and to reduce colonization by toxigenic *P. multocida* in the nares and tonsils of swine (Nielsen J P et al. 1991; Can J Vet Res 55(2):128-138). Thus, recombinant PMT derivatives may serve as ideal immunogens to elicit a good protective response without cytotoxicity in animals.

Formalin is the most common reagent used to inactivate PMT, but it may induce chemical alterations that can reduce the immunogenicity or efficacy of vaccines (Nielsen J P et al. 1991; as described). Therefore, a non-toxic but immunogenic PMT derivative could be advantageous to the development of effective vaccines against PAR. Most of the PAR vaccines tested to date consist of inactivated cultures of *P. multocida* or PMT toxoids. The toxoids are prepared by treatment of PMT with formaldehyde, which eliminates toxicity while maintaining antigenicity. These PAR vaccines are effective when tested on farms. However, PMT constitutes less than 0.6% of the total cellular proteins of *P. multocida* making it necessary to culture a large quantity of bacteria in order to obtain sufficient antigen for commercial scale use. Traditional toxoid vaccines require large scaled culture of a toxigenic strain of *P. multocida* and a tedious, expensive procedure for preparation of the PMT toxoid. In addition to being both time-consuming and expensive, the need to use inactivating reagents such as formaldehyde may induce uncontrollable chemical alterations in the immunogenicity of proteins that can reduce or eliminate the efficacy of such vaccines.

The N-terminal portion of PMT (residues 1 to 506 a.a.) has been considered to contain the putative cell binding domain and translocation domain. Immunization of the N-terminal rsPMT Tox1 (residues 1 to 487 a.a.) could elicit neutralizing antibodies that could prevent PMT from binding to the target cells and subsequently translocating across the cell membrane. Consequently, the PMT activity was blocked. In addition, the C-terminal portion of PMT was suggested as the catalytic domain and antibodies raised against C-terminal fragments (residues 681-1285 and 849-1285) were capable of inhibiting the mitogenic effect of PMT. The residues 1165 (cysteine), 1205 (histidine) and 1223 (histidine) were showed to be essential for the intracellular activity of PMT (Baldwin M R et al. 2004; 54(1):239-250; and Pullinger G D et al. 2001; Infect. Immun. 69: 7839-7850). The rsPMT derivatives are easy to produce and not cytotoxic so that no extra chemical inactivation is required before use. U.S. Pat. No. 6,110,470 disclosed polypeptide derivatives of *P. multocida* toxin comprising amino acid sequences identical to PMT but lacking amino acids 1043-1130 or lacking amino acids 1130-1285.

Therefore, in this invention, three recombinant subunit PMT (rsPMT) derivatives, representing the N-terminal (aa. 2-486), middle (aa. 486-986), and C-terminal (aa. 986-1281) portions of PMT, are produced and their immunogenicities are characterized by assessing the level of PMT-specific antibody secreting cells, the serum neutralizing antibody titers and the degree of lymphocyte proliferation in immunized mice and swine. The efficacy of these recombinant subunits as a vaccine was also evaluated in pregnant sows and their offspring by analysis of neutralizing antibody titers in colostrum and serum, and by monitoring the survival rate and the mean weight gain in piglets after PMT challenge.

SUMMARY OF THE INVENTION

One aspect of the present invention is to provide a vaccine for immunizing animal against progressive atrophic rhinitis (PAR), which comprises a combination of at least two fragments of recombinant subunit *Pasteurella multocida* toxins (rsPMT) each having an amino acid sequence that substantially corresponds to the 2-486, 486-986 or 986-1281 amino acid residues in SEQ ID No: 2.

In a preferred embodiment, the vaccine comprises a combination of the N-terminal (aa. 2-486) and C-terminal (aa. 986-1281) portions of PMT. In another embodiment, the vaccine comprises a combination of the middle (aa. 486-986) and C-terminal (aa. 986-1281) portions of PMT.

In one embodiment, the fragments of PMT are manufactured by host cell that has been transformed with a plasmid comprising the coding sequence of *Pasteurella multocida* toxin fragment 2-486, 486-986 and/or 986-1281. The host cell used herein may be prokaryotic or eukaryotic.

In the second aspect, the present invention provides a multivalent vaccine against progressive atrophic rhinitis (PAR), which comprises a combination of at least two fragments of recombinant subunit *Pasteurella multocida* toxins (rsPMT) each having an amino acid sequence that substantially corresponds to the 2-486, 486-986 or 986-1281 amino acid residues in SEQ ID No: 2 as the first component; and at least one antigen or epitope associated with another animal pathology. In one embodiment, the multivalent vaccine is used for preventing and/or treating progressive atrophic rhinitis (PAR) and pseudorabies (PR).

DETAILED DESCRIPTION

Figure 1:
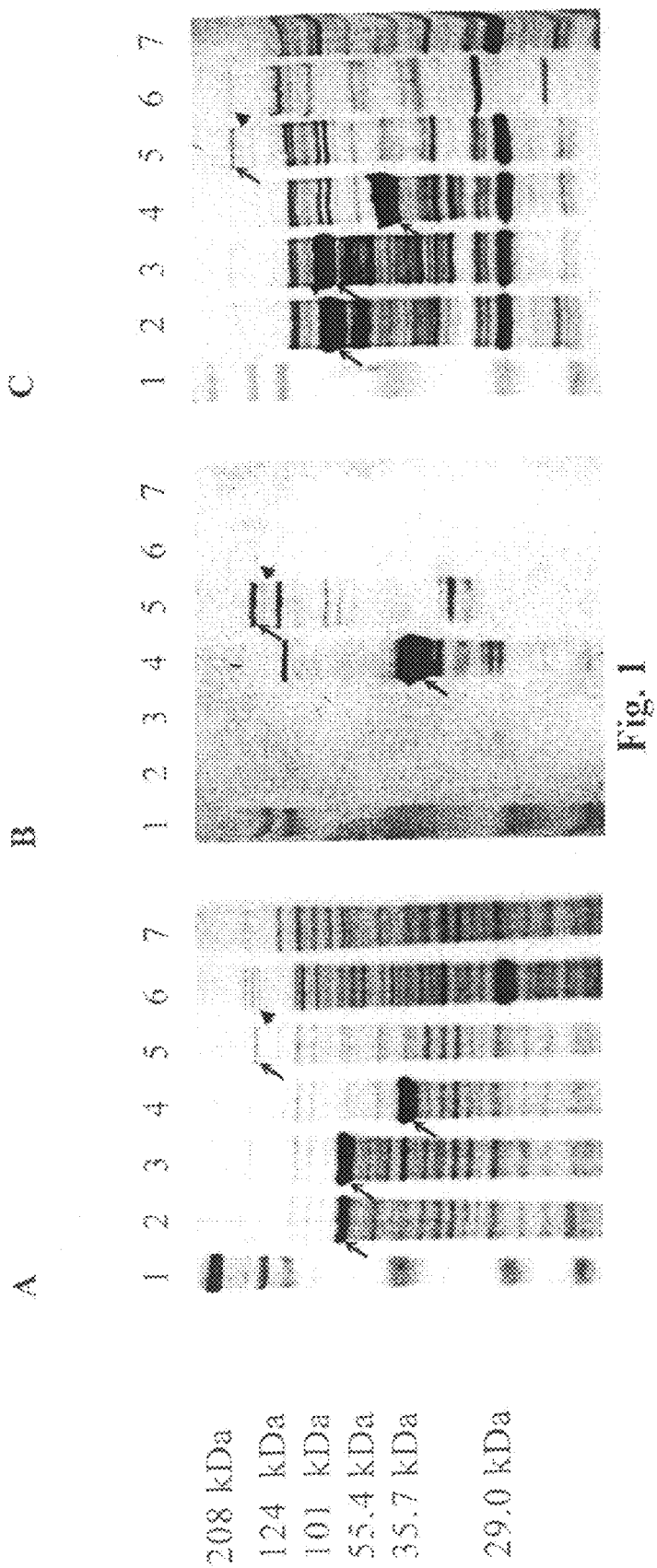
FIG. 1A-1C depict the total cellular proteins expressed by different rsPMT clones in *E. coli* were separated on 10% SDS-PAGE (A), followed by the Western blotting analysis using anti-PMT monoclonal antibody (B), or swine immune serum (C). Lane 1, protein standards (BIO-RAD); lane 2, Tox1 (86 kDa); lane 3, Tox2 (86 kDa); lane 4, Tox7 (55.4 kDa); lane 5, Tox6 (158 kDa); lane 6, PMT (155 kDa); lane 7, pET 32b(+). The location of each expressed rsPMT protein is indicated by an arrow, and native PMT synthesized in *P. multocida* PMD 48 is indicated by an arrowhead.

Unless defined otherwise, all technical and scientific terms used herein have the same meaning as is commonly understood by one of skill in the art of the invention. All patents and published lectures cited herein are incorporated by reference in their entirety.

The vaccine according to the present invention comprises a combination of at least two fragments of recombinant subunit *Pasteurella multocida* toxins (rsPMT) each having an amino acid sequence that substantially corresponds to the 2-486, 486-986 or 986-1281 amino acid residues in SEQ ID No: 2. The fragments of rsPMT may be expressed in prokaryotic or eukaryotic host cell transformed with a plasmid comprising the coding sequence of the *Pasteurella multocida* toxin fragments.

As used herein, a combination refers to any association between or among two or more elements.

As used herein, production by recombinant DNA technique by using recombinant DNA methods means the use of the well-known methods of molecular biology for expressing proteins encoded by cloned DNA.

As used herein, the term "vector" refers to a nucleic acid molecule capable of transporting another nucleic acid to which it has been linked. In general, expression vectors are in the form of "plasmid", which are generally circular double stranded DNA loops that are not bound to the chromosome.

As used herein, "amino acid residue" refers to an amino acid formed upon chemical digestion (hydrolysis) of a polypeptide at its peptide linkages.

Examples of conventional adjuvant used in the present vaccine formulations include Aluminum compounds, also known as aluminum gel, such as aluminum hydroxide, $Al(OH)_3$ and aluminum phosphate, $AlPO_4$; potassium aluminum sulfate, $KAl(SO_4)_2.12H_2O$ (D. E. S. Stewart-Tull (1996), Aluminum adjuvants. In Vaccine protocols, Robinson, A., G. H., and C. N. Wiblin, Farrar Human Press. Totoga, N.J., USA. pp. 135-139); Freund's complete adjuvant, FCA; Freund's incomplete adjuvant, FIA; water-in-oil, W/O emulsion; oil-in-water, O/W emulsion and the like.

Concanavalin A, Con A is an effective immunostimulant which activating T cells. The proliferative responses of T lymphocytes secrete IL-2 and other cytokines for promoting the associated immune responses.

EXAMPLES

Other features of the invention will become apparent in the course of the following descriptions of exemplary embodiments. These examples are given for illustration of the invention and are not intended to be limiting thereof.

Example 1

Construction of Derivative Clones of PMT

*Pasteurella multocida* PMD 48 is a type D toxigenic isolate obtained from a pig affected by a typical case of PAR in Taiwan (Liao C M et al. 2002; Taiwan Vet J 28(4):281-293.). *P. multocida* PMD 48 was cultured in Brain Heart Infusion (BHI) broth (Difco) for authentic *Pasteurella multocida* toxin preparation and genomic DNA extraction. The *E. coli* BL21 (DE3) strain (Novagen) was cultured in Luria-Bertain (LB) medium for cloning and protein expression. The PMT protein coding sequences were cloned into the T7 promoter-based pET expression vectors (Novagen). Restriction enzymes and T4 DNA ligase were purchased from New England Biolabs. A full-length PMT gene product was created by polymerase chain reaction (PCR) using PMT-specific primers (forward: 5'AGAGGTTATGGATCCGAAAACAAAA-CATTTT3', SEQ ID NO: 3; reverse: 5'CTCTTGT-TAAGCTAGCCTTTGTGAAAAGAGGAG3', SEQ ID NO: 10). The full-length gene product was purified and then digested with appropriate combinations of restriction enzymes to produce three different coding regions of the PMT gene. The 1459 bp BamHI/HindIII fragment encoding N-terminal amino acids 1-487 of PMT was cloned into pET32b to generate the Tox1 clone. The 1508 bp HindIII/HindIII fragment encoding the middle region (aa 485 to 987) of PMT was cloned into pET32a to generate the Tox2 clone, The 891 bp HindIII/NheI fragment encoding the C-terminal region (aa 986 to 1282) of PMT was cloned into pET25b and followed by subcloning the BamHI/BlpI fragment into pET32b to generate the C-terminal Tox7 clone. Recombinant expression plasmids Tox1, Tox2, and Tox7 were transformed into *E. coli* BL21 (DE3) according to the manufacturer's manual. The rsPMT expression was induced with 1 mM Isopropyl-β-D-thiogalactopyranoside (IPTG; Protech), and rsPMT was purified using the HIS BIND® Kits (Novagen, Darmstadt, Germany) according to the manufacturer's manual. The protein concentration was quantified using the Bio-Rad Protein Assay reagent (BIO-RAD, Hercules, Calif.). Authentic PMT was prepared from *P. multocida* PMD 48 cultured in BHI medium at 37° C. for 26 h as previously described (Nakai T et al. 1984; Infect Immun 46(2):429-434). The authentic PMT was detoxified with 0.3% (v/v) formalin (Fisher) at 37° C. with shaking for 48 h to generate PMT toxoid.

Example 2

Expression and Purification of rsPMT

The rsPMTs were expressed as fusion proteins containing an N-terminal fusion peptide. Plasmids Tox1, Tox2, Tox6 and Tox7 were transformed into competent *E. coli* BL21 (DE3) cells according to the manufacturer's instructions. A single colony of each transformant was grown at 37° C. in Luria-Bertain (LB) medium containing 100 µg/ml ampicillin until the $OD_{600}$ reached 1.0. Isopropyl-β-D-thiogalactopyranoside (IPTG) was then added to a final concentration of 1 mM. The culture was incubated for an additional 6 hr at 37° C. The cells were, harvested by centrifugation and resuspended in phosphate buffered saline (PBS) with 0.1% Triton X-100. Cells were broken by sonication and the suspension were mixed with an equal volume of 2×SDS-PAGE sample buffer (125 mM Tis-HCl [pH 6.8], 20% glycerol, 4% SDS, 10% β-mercaptoethanol, 0.25% bromophenol blue) and the proteins were separated by SDS-PAGE. Native PMT was prepared from *P. multocida* PMD 48 cultured in BHI medium at 37° C. for 26 hr as previously described in the report of Nakai T et al. After cells were broken, the insoluble fractions containing rsPMTs were harvest by the centrifugation. The insoluble fractions were dissolved in solubilization buffer (50 mM CAPS, 0.3% N-lauroylsarcosine, 1 mM DTT; Novagen, Darmstadt, Germany) and incubated at room temperature for 15 min. After centrifugation, supernatant containing the solubilized protein was transferred to a clean tube for further recombinant protein purification. The rsPMT was purified using the HIS BIND® Kits (Novagen, Darmstadt, Germany) according to the manufacturer's manual, followed by refolding in 10-fold volumes of PBS at 4° C. overnight. After concentrated with AMICON® Ultra 30,000 MWCO (Millipore, Bedford, USA), the protein concentration was quantified using the Bio-Rad Protein Assay reagent (BIO-RAD, Hercules, Calif.).

Figure 2:
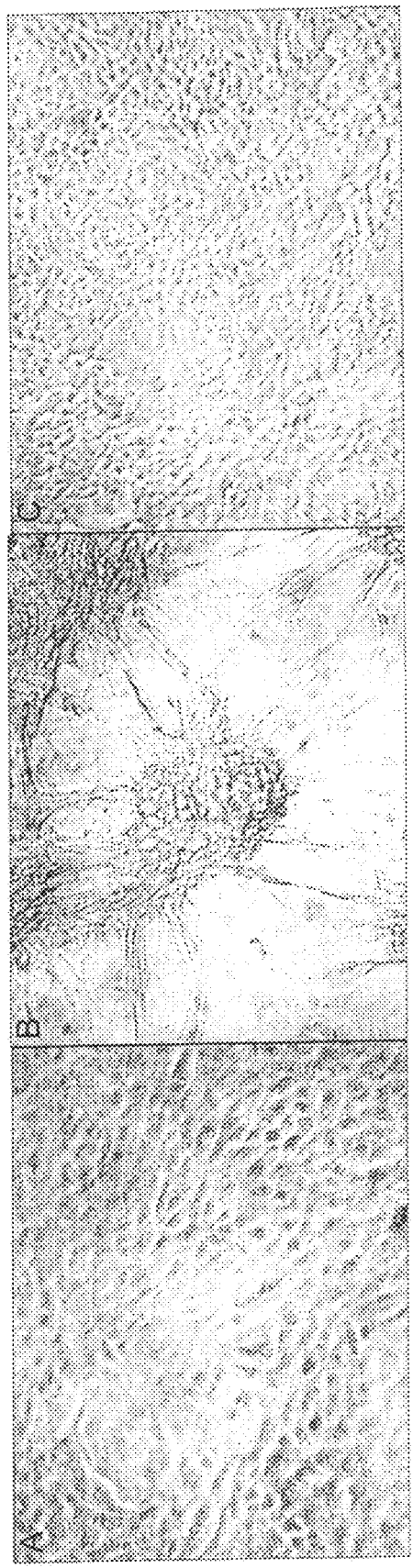
FIG. 2A-2C depict the cytotoxicity of rsPMT and native PMT on Vero cells. Monolayers of Vero cells were treated with DMEM (A), 140 ng/ml native PMT (B), and 1.5 mg/ml Tox1 (C), respectively at 37° C. for 7 days. The cellular morphology is visualized by the phase-contrast microscope (Olympus IX-70). Magnification 100×.

Three recombinant subunit PMT proteins representing the N-terminal (Tox1; aa 1 to 487), the middle (Tox2; aa 485 to 987), and C-terminal (Tox7; aa 986 to 1282) regions of PMT, respectively, were successfully produced in *E. coli*. The molecular weight of Tox1, Tox2, and Tox7 on 10% SDS-PAGE was 86, 86, and 55.4 kDa, respectively (FIG. 2). The expression efficiencies of rsPMT proteins ranged from 28-35% of the total cellular protein (data not shown). The expression of rsPMT was remarkably increased up to 60 fold in the total cellular proteins. These results suggest that, as compared with production of native PMT, sufficient quantities of rsPMT proteins could be obtained to significantly decrease the costs of vaccine preparation.

Example 3

Cytotoxicity Assay of rsPMT in Mice

African green monkey kidney cells (Vero, ATCC CCL-81) were obtained from Food Industry Research and Development of Taiwan, R.O.C. and cultured in DMEM supplemented with 2 mM L-glutamine, 1.5 g/l sodium bicarbonate, 0.1 mM sodium pyruvate and 5% fetal calf serum (FCS, Gibco/BRL). Vero cells were seeded into the wells of 96-well plates (Costar) at a density of 5×10⁴ cells per well and the plates were incubated at 37 C overnight. Serial dilutions of rsPMT or native PMT proteins were added to the cell monolayers and the cells were incubated in DMEM containing 2% FCS at 37° C. for 5-7 days. Cytopathic effects consisting of nodular formation in the monolayer were visualized by phase-contrast microscope (Olympus IX-70) and the minimal toxic dose (MTD) was calculated for each rsPMT and the native PMT. All of the rsPMT were non-cytotoxic (FIG. 3), even at dosages as high as 1.5 mg/ml. In contrast, the minimal toxic dose (MTD) of native PMT was 140 ng/ml, which was at least 10000-fold more toxic to Vero cells than any of the rsPMT proteins.

$LD_{50}$ in mice. Fifty SPF BALB/c mice were randomly grouped and each mouse was inoculated via intraperitonal (i.p.) injection with 0.5 ml of a suspension containing a selected concentration of rsPMT or native PMT at six-week-old. These mice were observed for 14 days after inoculation and mortality was recorded. The $LD_{50}$ was determined by the 50% end-point method of Behrens-Kärber. Mice inoculated with native PMT demonstrated rough hair coat, anorexia and reluctance to move. These animals huddled in the corners of cages and died within 2-3 days. Lesions at necropsy included congestion or hyperemia of organs and atrophy of spleen. The $LD_{50}$ of native PMT in BALB/c mouse was 1.30 µg. In contrast, no significant clinical symptoms, gross lesions or other pathological findings were observed in mice receiving doses as high as 1 mg of rsPMT proteins (Table 1).

TABLE 1

The expression efficiency of native and recombinant subunit PMT, and their 50% lethal dose ($LD_{50}$) in BALB/c mouse

| | Recombinant subunit PMT | | | | Native PMT |
|---|---|---|---|---|---|
| | Tox1 | Tox2 | Tox6 | Tox7 | |
| Recombinant protein/total cellular protein (%)[a] | 28.2 ± 5.07 | 35.8 ± 6.88 | 4.1 ± 0.41 | 32.1 ± 6.92 | 0.6 ± 0.15 |
| $LD_{50}$ (µg/0.5 ml)[b] | >1000 | >1000 | ND | >1000 | 1.30 |

[a]The expression efficacy was analyzed with AlphaImager™ 2200 image system.
[b]$LD_{50}$ was presented as the protein concentration needed to kill 50% of mice.

Example 4

Immunoprotective Properties of the rsPMT Proteins in Mice ELISPOT of Antibody Secreting Cells A suspension of mouse spleen MNCs was assayed for PMT-specific ASCs by the enzyme-linked immunospot (ELISPOT) assay. The 96-well nitrocellulose bottomed plates (Millititer HA, Millipore Corp) were coated with rsPMT (100 ng/ml) and incubated at 4 C overnight. The plate was washed with PBS containing 0.05% Tween-20 (PBS-T) and blocked with PBS containing 0.5% bovine serum albumin. Following incubation at 37 C for 1 hr, the plate was washed once with PBS-T and incubated with serial dilutions of a suspension of MNCs. Cells were incubated at 37 C in an atmosphere containing 5% $CO_2$ for a further 6 hr. The plate was washed once with PBS-T, followed by reacting with PBS-diluted alkaline phosphatase-conjugated goat anti-mouse IgG at 37 C for 1 hr. Finally, the plate was washed six times with PBS-T, and reacted with a chromogen/substrate solution NBT/BCIP (Sigma) at room temperature for 15 to 20 min. After rinsing with deionized water, the color spots present on each well were visualized and quantified with stereomicroscope.

Figure 3:
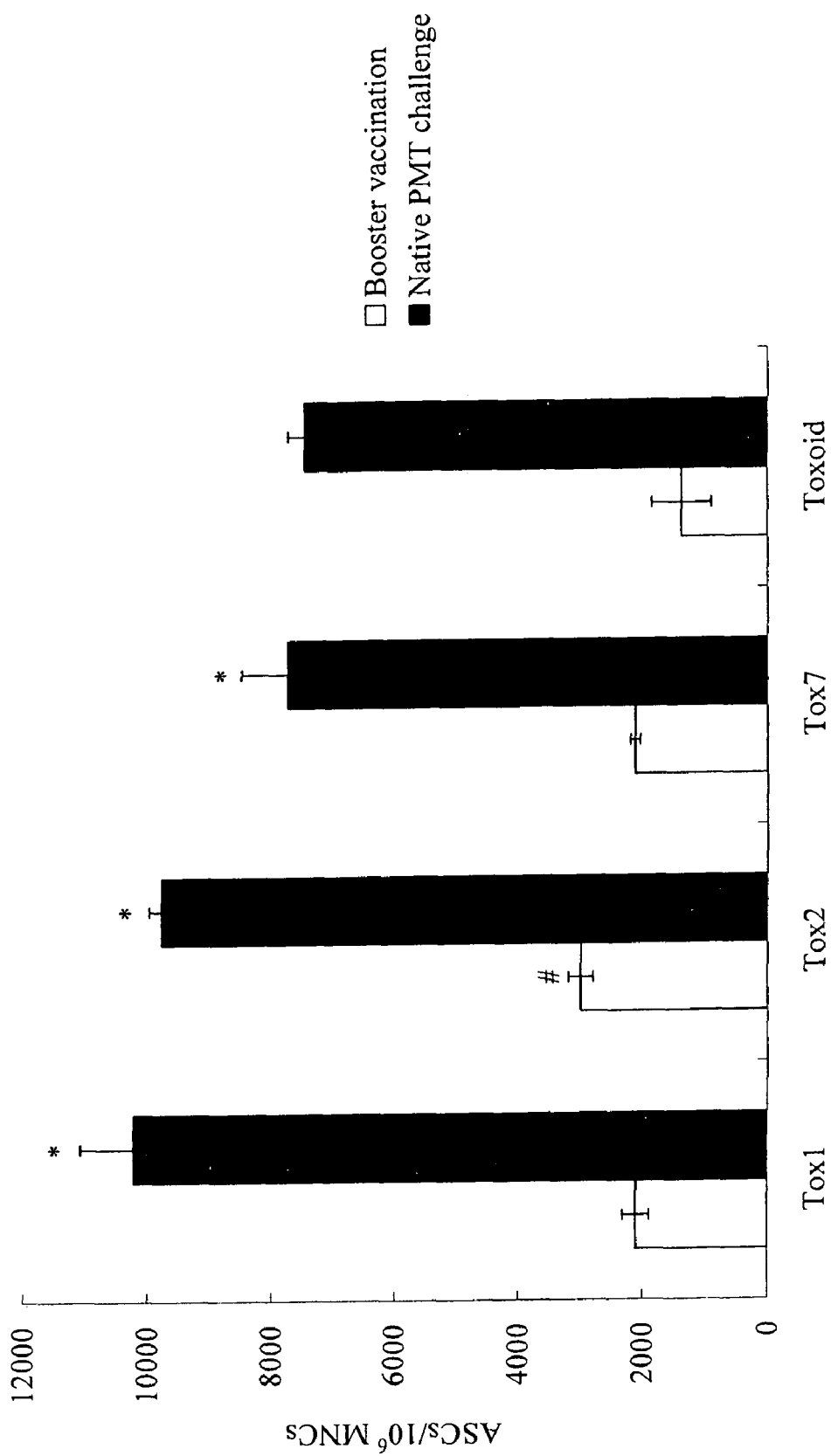
FIG. 3 depicts the PMT-specific ASCs of immunized mice present in spleen at 14 days post booster vaccination (open bars) and lethal dose of native PMT challenged (closed bars). At each time point, 3 mice/group were studied. #Significantly ($p<0.05$) different with toxoid-immunized mice after booster vaccination. *Significantly ($p<0.05$) different with toxoid-immunized mice after native PMT challenged.

The mouse spleens were markedly enlarged following the second immunization. Two weeks following challenge with native PMT, the spleens from Tox1- and Tox2-immunized mice began to atrophy, but all of the mice survived. The greatest numbers of ASCs were detected in the Tox2-immunized mice possessing 2993.33±200.33 ASCs specific to PMT in $10^6$ MNCs. The lowest amount of ASCs (1386.67±477.21 in $10^6$ MNCs) was detected in the PMT toxoid-immunized mice. Except Tox2-immunized mice, there was no significant difference among the Tox1-, Tox7- and toxoid-immunized mice (p<0.05). The ASCs of immunized mice increased significantly in every group after challenge with native PMT (p≦0.001) (FIG. 3). The Tox1-immunized mice demonstrated the greatest increase in the number of ASCs with 10233.33±850.49 in $10^6$ MNCs (FIG. 3).

Cellular Response of Immunized Mice

Anti-PMT cellular immune response of mice was analyzed by a lymphocyte proliferation assay. The mean stimulation indices of Tox1-, Tox2-, Tox7-, and toxoid-vaccinated mice were 2.11±0.27, 3.31±0.95, 2.31±0.26, and 6.02±0.68, respectively. After challenge with native PMT, only the cells isolated from Tox7- and toxoid-immunized mice could be stimulated with native PMT in vitro. The results implied that mice vaccinated with rsPMT proteins could mount a specific cellular response against PMT (SI>2), but the response might be inhibited by exposure to native PMT (Table 2).

TABLE 2

Lymphocyte proliferation assay of immunized mice at 14 days post booster vaccination and lethal dose of native PMT challenge

| Grouping | Booster vaccination (n = 3) | PMT Challenge (n = 3) |
|---|---|---|
| Mock | 0.99 ± 0.26 | 1.66 ± 0.49 |
| Tox1 | 2.11 ± 0.27 | 1.06 ± 0.49 |
| Tox2 | 3.31 ± 0.95 | 0.96 ± 0.19 |
| Tox7 | 2.31 ± 0.26 | 2.8 ± 0.37 |
| Toxoid | 6.02 ± 0.68 | 8.07 ± 4.13 |

Data were expressed as the stimulation index (SI).
SI = cpm in antigen stimulated cultures/cpm in unstimulated cultures.
An SI value greater than 2 was regarded as positive (van Diemen et al., 1994)

Example 5

Figure 4A:
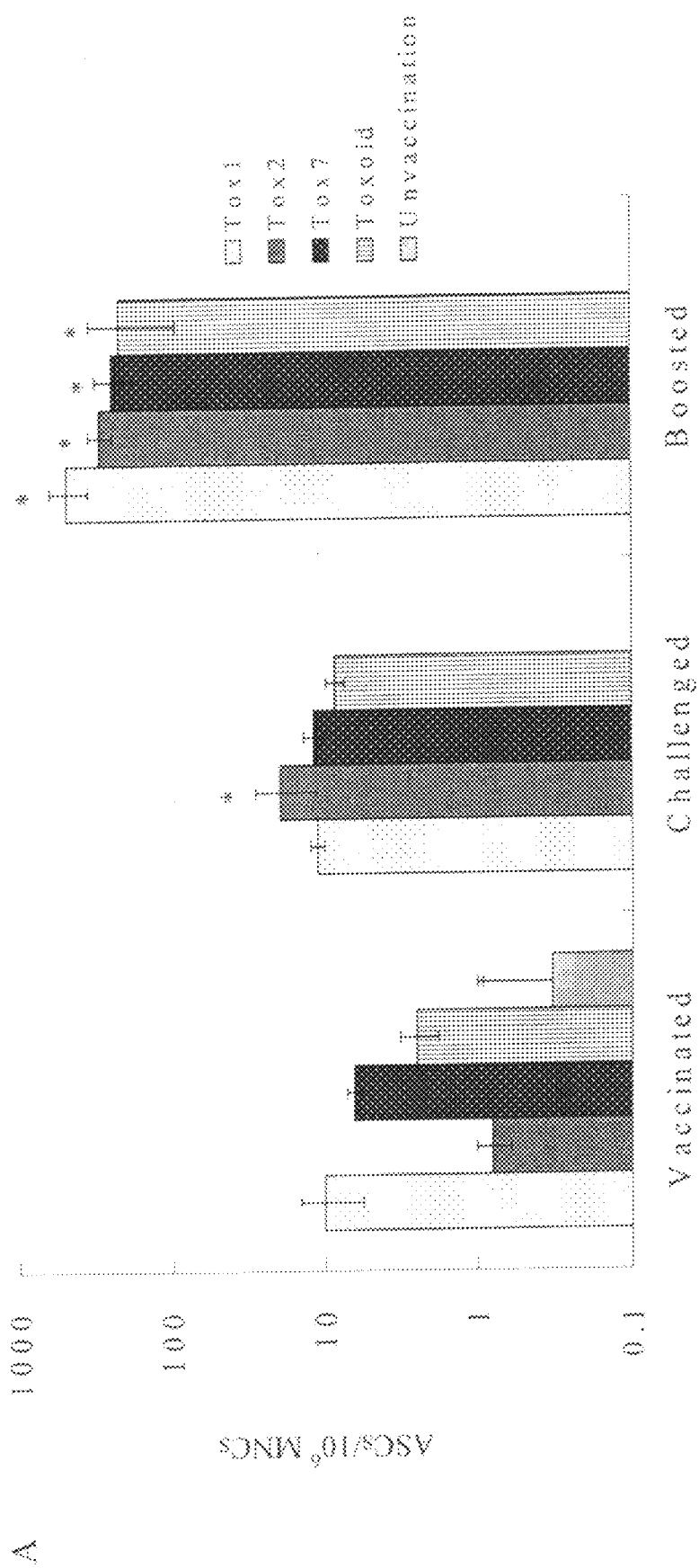
FIG. 4A-4B depict PMT-specific ASCs detected in pulmonary lymph node (A) and spleen (B) of piglets after booster immunization (vaccinated), and subsequent PMT challenge (challenged) or homologous antigen booster (boosted). The results of each experiment were analyzed for effect of treatment using Student's t distribution. Statistical results were considered to be significant when p-values were lower than or equal to 0.05 (*).
Figure 4B:
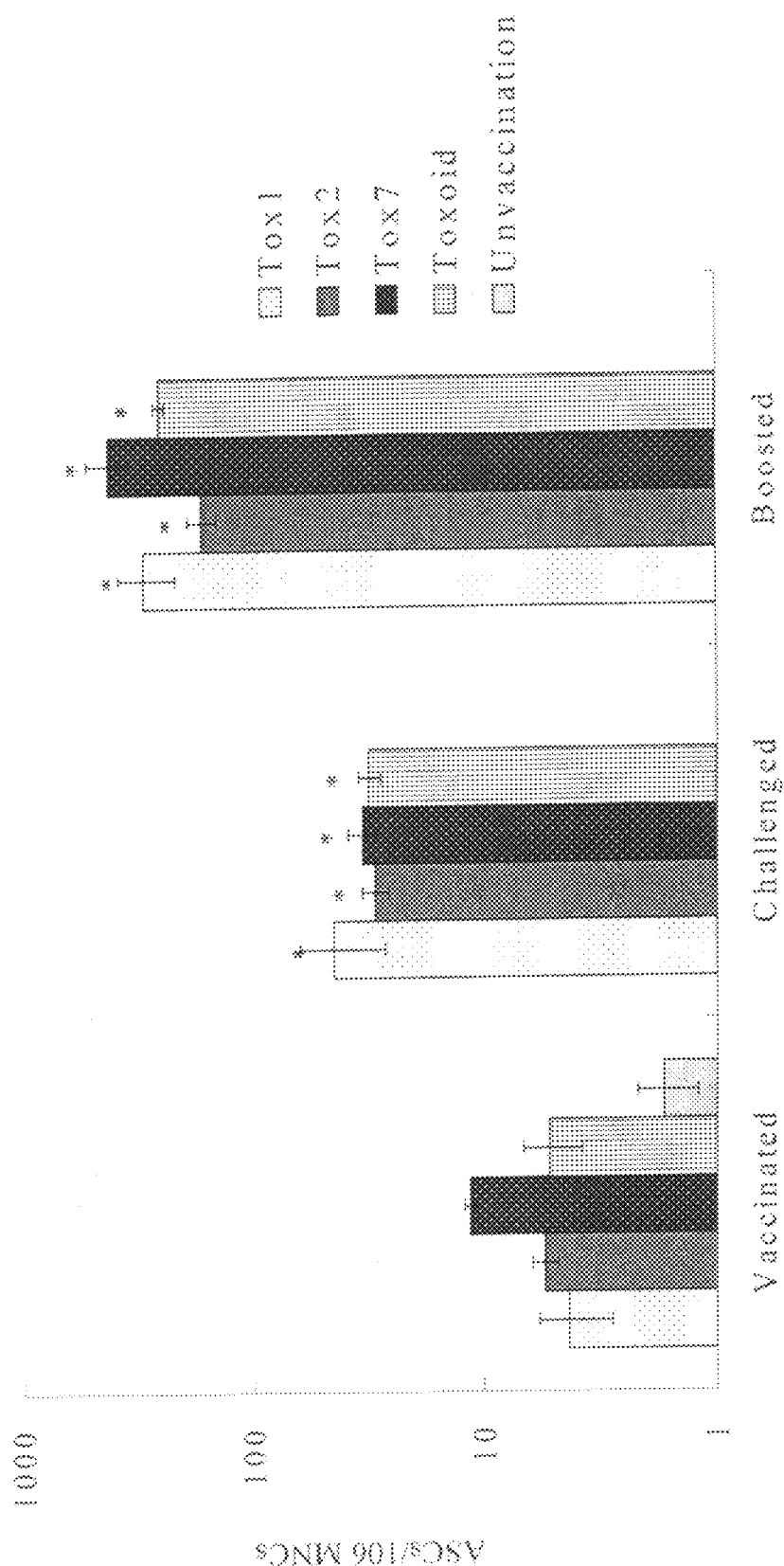

Protection Efficacy of rsPMT Vaccine in Pigs
Antibody Responses in Immunized Piglets The antigenicity of the rsPMT products was tested in 4-week-old piglets by analyzing the level of PMT-specific antibody secreting cells and titers of neutralizing antibodies after immunization, PMT challenge, or homologous antigen booster. The spleen and pulmonary lymph node antibody secreting cells were quantified by ELISPOT assay. Each staining spot represented one PMT-specific ASC, and total color spots were quantified. Only a few PMT-specific ASCs were detected at 14 days after booster vaccination in each vaccinated group. The greatest number of PMT-specific ASCs in the spleen was detected in Tox7-immunized piglets that had 11.5±0.7 ASCs per $10^6$ MNCs (see, FIG. 4B), and the greatest number of PMT-specific ASCs in lymph nodes was shown in the Tox1 group (FIG. 4A). The amounts of ASCs increased slightly at 4 weeks after authentic PMT challenge, but increased dramatically in the group booster with homologous antigen. The Tox1-immunized piglets demonstrated the greatest increase in ASCs with 493.3±138.7 per $10^6$ MNCs in pulmonary lymph node and Tox7-immunized piglets possessed the greatest increase in ASCs with 440±104.4 per $10^6$ MNCs in spleen MNCs after antigen booster (showed in FIG. 4).

Figure 5:
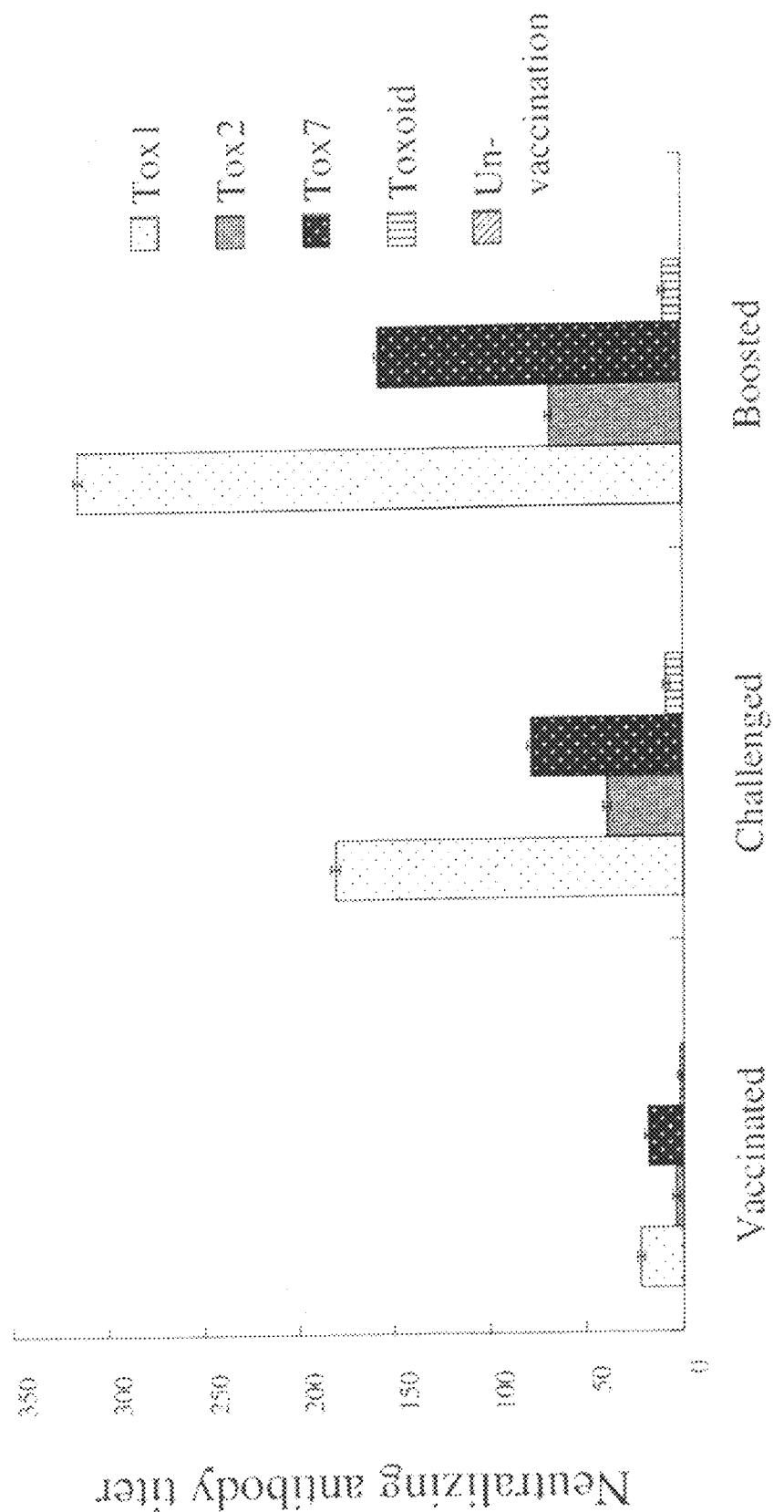
FIG. 5 depicts PMT-specific serum neutralizing antibody titers in piglets after boost immunization (vaccinated), and subsequent PMT challenging (challenged) or homologous antigen booster (boosted). The SN titer was expressed as the end-point dilution of serum that could inhibit the cytotoxicity of 4-fold MTD of authentic PMT on Vero cells.

Furthermore, the PMT-specific neutralizing antibody titer was determined as its ability to inhibit the cytopathic effects induced by PMT in Vero cells. After booster vaccination, moderate levels of neutralizing antibody titer ($\geq 1:16$) were detected in Tox1- and Tox7-immunized pigs, and a low level of neutralizing antibody titer (1:4) was detected in Tox2 group. The neutralizing antibody titers increased significantly after PMT challenge or booster with homologous rsPMT antigen, but not in the PMT toxoid vaccinated group. The Tox1 immunized pigs could generate the highest neutralizing antibody titers in every assay point and the Tox7-immunized pigs were the next. There was no detectable neutralizing antibody in unvaccinated pigs. In summary, after PMT challenge or homologous antigen booster, the neutralizing antibody titers in recombinant subunit PMT immunized pigs could reach 1:32 to 1:512, but only 1:8 in PMT toxoid immunized pigs (FIG. 5).

Cellular Immune Response in Immunized Piglets

The specific cellular immune response to each recombinant subunit PMT was analyzed by the lymphocyte proliferation assay. Lymphocyte proliferation was measured and presented as the stimulation index (SI). After booster vaccination, a PMT-specific lymphocytes proliferation in spleen was observed in Tox2- and Tox7-vaccinated pigs as indicated with a SI greater than 2, while no response was detected in pulmonary lymph node. After PMT challenge or homologous antigen booster, the spleen MNCs from each rsPMT or toxoid immunized group all demonstrated significant enhancement of lymphocyte proliferation (Table 3). Except for Tox1-immunized pigs, the pulmonary lymph node MNCs in each group also showed specific proliferation response after homologous antigen booster.

TABLE 3

PMT-specific proliferation of lymphocytes in MNCs from pulmonary lymph nodes (PLN) and spleen isolated from immunized piglets after booster vaccination, challenged with PMT, and boosted with homologous antigen

| Group (Vaccination antigen) | Vaccination | | PMT challenge | | Homologous antigen booster | |
|---|---|---|---|---|---|---|
| | PLN | Spleen | PLN | Spleen | PLN | Spleen |
| Tox1 | 1.1 | 1.0 | 1.2 | 5.6 | 1.8 | 4.8 |
| Tox2 | 1.2 | 4.0 | 1.9 | 4.9 | 3.1 | 5.1 |
| Tox7 | 1.4 | 3.4 | 1.4 | 3.5 | 4.2 | 4.6 |
| Toxoid | 1.5 | 1.8 | 1.0 | 6.9 | 4.0 | 5.6 |

Data are average of the stimulation index (SI) of PMT-specific lymphocyte proliferation form three pigs at each time point. The SI was calculated as described in Materials and Methods, and SI > 2 represent lymphocyte proliferation.

Protection Efficacy of rsPMT Vaccine in Piglet

To evaluate the protection efficacy of these rsPMTs in newborn piglets, immunization of the pregnant sows with rsPMTs mixture with or without *P. multocida* type A bacterin and a conventional PAR-toxoid vaccine were applied for comparison. The neutralizing antibody titers in sows' colostrum were assayed at parturition and the maternal neutralizing antibody titers in sera from offspring were analyzed at one-day of age. Pregnant sows vaccinated with rsPMTs then given (group A) or not given (group B) an injection of *P. multocida* type A bacterin could mount a significant response with high neutralizing antibody titers in colostrum ($\geq 1:80$) that could be transferred successfully to newborn piglets (Table 4). Immunized sows in group A demonstrated a higher antibody response than those in group B. By contrast, the conventional PAR-toxoid vaccine (group C) induced a medium level of neutralizing antibody leading to low antibody titers in their offspring (1:8). Only basal levels of neutralizing antibody titer ($\leq 1:4$) were detected in the control animals (group D). In addition, ten offspring from each group at 14-day-old were challenged by intramuscular injection with 200 μg/kg (5-fold lethal dose) of authentic PMT. The death of piglets was observed as early as 24 h post-inoculation in groups C and D, but not until 4th days post-inoculation in groups A and B. The survival rates of offspring from groups C and D were 0% but reached 60% in groups A and B at 28-days of age (Table 4).

TABLE 4

Neutralizing antibody titers of immunized sows and their offspring, and the survival rate of offspring after challenged with a 5-fold lethal dose (200 μg/kg) of authentic PMT at 14-day-old

| | | Mean neutralizing antibody titer | | | |
|---|---|---|---|---|---|
| Group | Vaccine composition | Sows Colostrums | Newborn 1-day-old | Piglets 28-day-old | Survival rate[a] |
| A | rsPMTs + *P. multocida* bacterin | 1:101 | 1:102 | 1:2 | 60% |
| B | rsPMTs | 1:80 | 1:79 | 1:2 | 60% |
| C | Conventional AR-toxoid vaccine | 1:39 | 1:8 | ND[b] | 0% |
| D | Unvaccinated | 1:4 | 1:2 | ND[b] | 0% |

[a]Survival rate was calculated at 28-day-old.

[b]Not determined, all piglets were dead within 24 h after PMT challenge.

Figure 6:
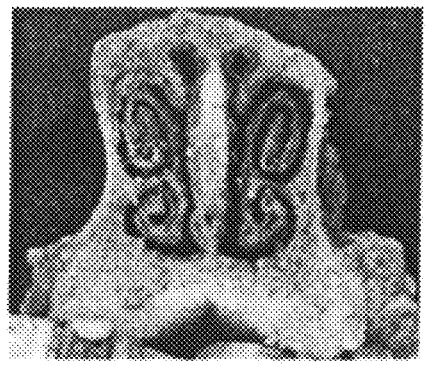
FIG. 6A-6D depict the representative photographs of the turbinate conchae of experimental pigs in groups vaccinated with rsPMTs vaccine (B), conventional AR-toxoid vaccine (C), and unvaccinated (D), at 2-weeks after authentic PMT challenge. The unvaccinated and unchallenged pigs were served as the negative control (A).
Figure 6:
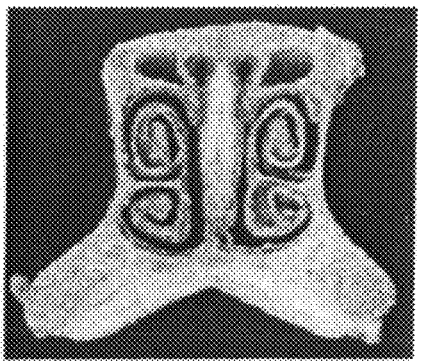
Figure 6:
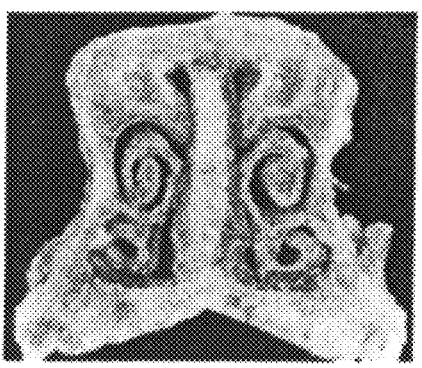
Figure 6:
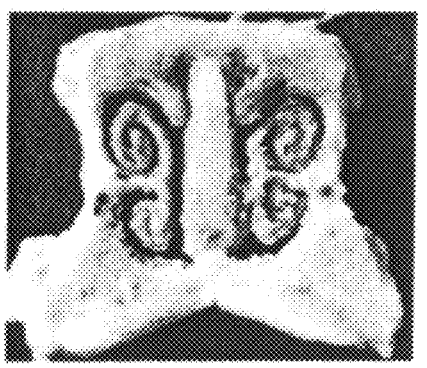
Figure 6:
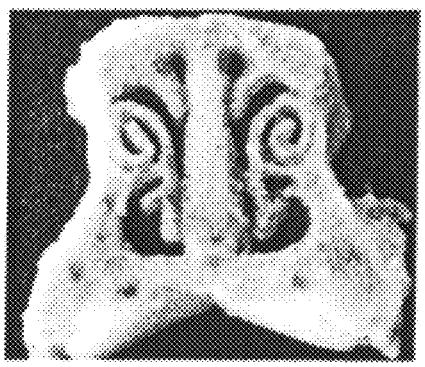
Figure 6:
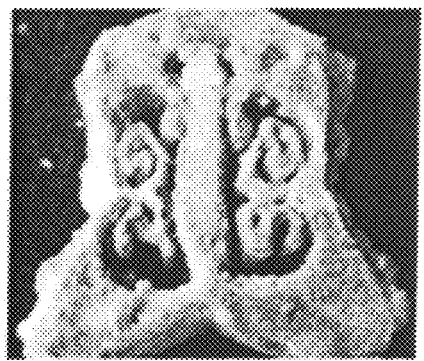

Furthermore, another twenty offspring from each group were tested for weight gain. Half of the piglets in each group were challenged with 30 μg/kg (sublethal dose) of authentic PMT via intramuscular injection at 14-days of age, and the remaining half were untreated. The mean body weight gain of piglets was recorded at 14 days post-inoculation. There was no significant difference among the piglets from three vaccination groups, either challenged or unchallenged, but a significant reduction in weight gain ($p<0.05$) was observed among piglets in the control group D that were challenged with authentic PMT compared with their unchallenged cohort (Table 5). In the nasal conchal gross examination, there were low levels of turbinate atrophy with scores ranged from 0.1 to 0.3 in the piglets from sows vaccinated with rsPMTs, even after these piglets were challenged with authentic PMT. In contrast, after authentic PMT challenge, piglets from the conventional AR-toxoid vaccinated and unvaccinated sows showed mild to severe turbinate atrophy with average scores of 1.4 and 3.4, respectively (see, Table 5; and FIG. 6), which were significantly different from rsPMTs vaccinated groups ($p<0.05$).

TABLE 5

Mean weight gain and turbinate conchal score of the offspring piglets after 2 weeks challenged with subleathal dose (30 μg/kg) of authentic PMT

| Sows group | Vaccine composition | Mean weight gain of piglets (mean ± SD) (kg) | | Mean score of turbinate conchal atrophy[a] | |
|---|---|---|---|---|---|
| | | Unchallenged | Challenged | Unchallenged | Challenged |
| A | rsPMTs + P. multocida bacterin | 3.9 ± 0.8 | 3.5 ± 0.4 | 0.1 | 0.2 |
| B | rsPMTs | 5.0 ± 0.6 | 4.5 ± 1.3 | 0.2 | 0.3 |
| C | Conventional AR-toxoid vaccine | 4.4 ± 1.0 | 3.5 ± 0.9 | 0.2 | 1.4[#] |
| D | Unvaccinated | 5.2 ± 0.3 | 3.5 ± 0.8* | 0.2 | 3.4[#] |

[a]The degrees of turbinate conchal atrophy were ranged from 0 (normal) to 4 (complete atrophy)
*The mean daily weight gain in control group differs significantly (t-test, $p < 0.05$)
[#]The mean score of turbinate conchal atrophy in control group differs significantly (t-test, $p < 0.05$)

There was no significant difference in weight-gain between the toxin-challenged and unchallenged subgroups, but piglets from unvaccinated sows showed poorer growth performance after PMT challenge than those unchallenged ($p<0.05$). In addition, piglets from sows vaccinated with rsPMTs mixture with or without P. multocida type A bacterin exhibited low level of turbinate conchal atrophy after challenged with authentic PMT. In contrast, piglets from the conventional PAR-toxoid vaccinated and unvaccinated sows showed significant atrophy of turbinate conchae. These results indicated that an effective vaccination of sows during pregnancy could protect offspring against PAR.

In conclusion, vaccination with the short fragments of recombinant subunit PMT proteins resulted in high levels of neutralizing antibody and a specific cellular immune response against PMT in swine. Immunization of sows with recombinant subunit PMT vaccine during pregnancy is safe and able to elicit levels of neutralizing antibodies in colostrum that could protect their offspring against PMT. These non-toxic recombinant subunit PMT proteins hold great potential as suitable antigens in developing an effective subunit vaccine against PAR.

Example 6

Preparation and Immunogenicity Test of the Bivalent Vaccine (PAR-PR) Against Progressive Atrophic Rhinitis and Pseudorabies The PAR vaccine (comprising 2.1 mg PMT recombinant subunit proteins, each 0.7 mg, 1×10$^9$ CFU of inactivated P. multocida serotype A, and 1×10$^9$ CFU of inactivated P. multocida serotype D) was mixed with inactivated gE-deleted pseudorabies virus (10$^8$ TCID$_{50}$), and then the sterile oily adjuvant (W/O/W type) or aluminum gel was added to the mixture to form a PAR-PR bivalent vaccine formulation of 2-ml and 4-ml dosage.

Immunoprotection of PAR-PR Bivalentvaccine in Pregnant Sows

Figure 7:
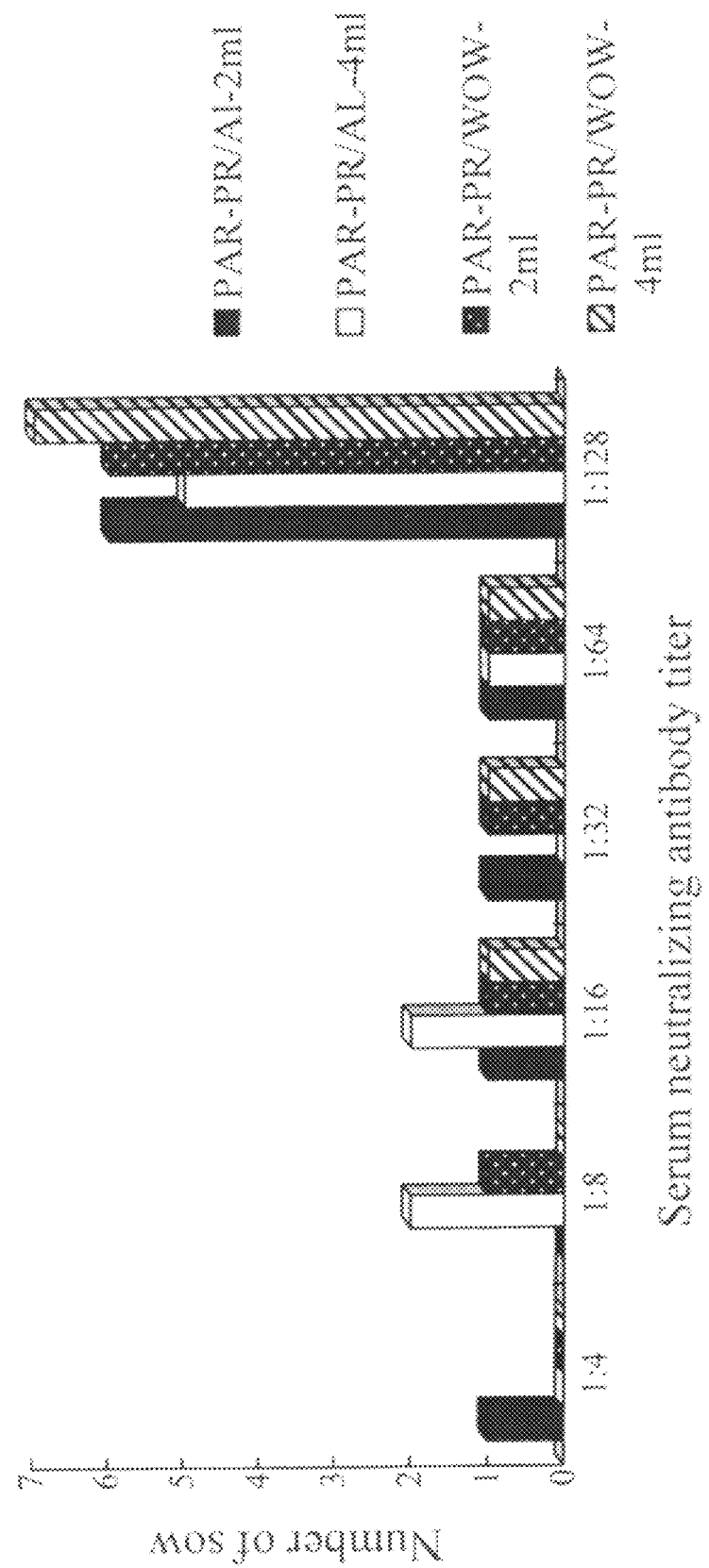
FIG. 7 depicts the PMT-specific serum neutralizing antibody titers in pregnant saws before and after boost immunization (vaccinated) of the PAR-PR bivalent vaccine.
Figure 8:
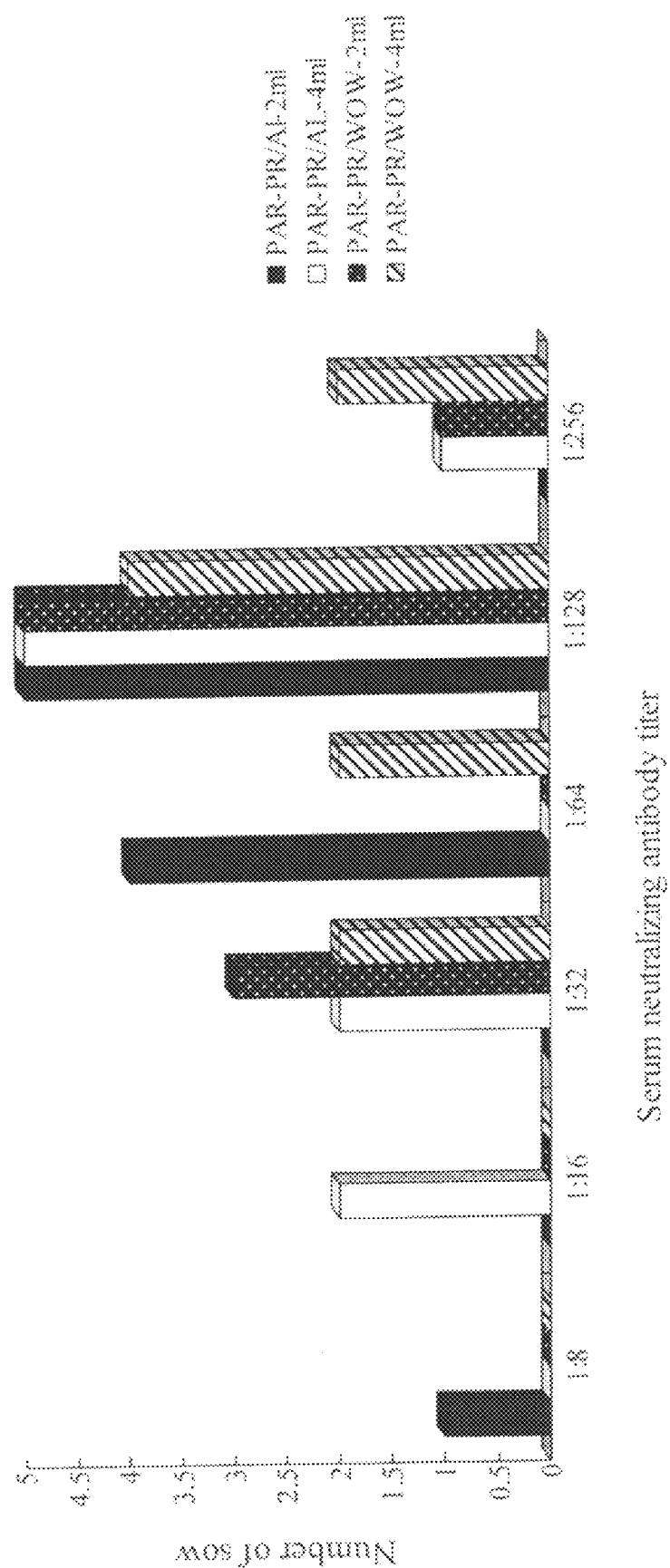
FIG. 8 depicts the PR-specific serum neutralizing antibody titers in pregnant sows before and after boost immunization of the PAR-PR bivalent vaccine.

The pregnant sows were immunized by intramuscularly injecting with the PAR-PR bivalent vaccine formulation comprising aluminum gel or oily adjuvant in 2-ml and 4-ml dosage respectively and collected blood samples for the detection of PMT- and PR-specific serum neutralizing antibody titers. As showed in FIGS. 7 and 8, the average PMT and PR neutralizing antibody titers observed in sows immunized with the 2-ml dosed aluminum gel containing bivalent vaccine were 88.4- and 90.4-folds respectively, and of 75.2 and 99.2-folds observed in the 4-ml dosage treated sows. Of the observation in oily adjuvant containing bivalent vaccine treated animals, the average PMT and PR neutralizing antibody titers detected were 88.8- and 92.8-folds in 2-ml dosage groups, respectively. In 4-ml dosage groups, the average PMT neutralizing antibody titer detected was 101.2-folds and the RP neutralizing antibody titer was 110.5-folds.

---

The invention claimed is:

1. A method of making a composition, which comprises: (a) separately cloning the DNA fragment coding *Pasteurella multocida* toxin (rPMT) subunits with amino acid residues 1-487 in SEQ ID NO: 2 into pET32b expression vector, cloning the DNA fragment coding *Pasteurella multocida* toxin (rPMT) subunits with amino acid residues 485-987 in SEQ ID NO: 2 into pET32a expression vector, and cloning the DNA fragment coding *Pasteurella multocida* toxin (rPMT) subunits with amino acid residues 986-1282 in SEQ ID NO: 2 into pET32b expression vector to obtain three recombinant plasmids; (b) transforming each of the recombinant plasmids into an *E. coli* BL21 (DE3) strain for the expression of the *Pasteurella multocida* toxin (rPMT) subunits Tox1, Tox2, and Tox7; (c) harvesting and purifying the recombinant rPMT subunits from the transformant cell cultures; and (d) combining the purified recombinant rPMT subunits in an adjuvant.

2. The method of claim 1, which further comprises the step of mixing at least one antigen derived from PMT toxoid, serotype A *Pasteurella multocida*, serotype D *Pasteurella multocida* or *Bordetella bronchiseptica* into the composition.

3. The method of claim 1, wherein the adjuvant is selected from Freund's complete adjuvant, Freund's incomplete adjuvant, aluminum gel,. oily adjuvant (W/O/W), water-in-oil (W/O) emulsion, oil-in-water (O/W) emulsion, ConA, β-glucosan, and a combination thereof.

* * * * *

SEQUENCE LISTING

<160> NUMBER OF SEQ ID NOS: 13

<210> SEQ ID NO 1
<211> LENGTH: 4380
<212> TYPE: DNA
<213> ORGANISM: P. multocida strain X-73
<220> FEATURE:
<221> NAME/KEY: CDS
<222> LOCATION: (219)..(4076)

<400> SEQUENCE: 1
aacaagggaa aatagctaga ttagacgata tcgataatat cataaataat atttaaaaat     60

```
tacgccccctt gacctagagg ggcttttttta ttacatcaaa aaaataaacc caaacactgc    120
gaatgtttgg ggttttattt ataaccaaaa tacattaata tgtttattaa gtaagcatta    180 tcttactttta ggaataaact aacatagagg ttatggatat gaaaacaaaa catttttttta    240 actcagattt tactgtaaaa ggaaaaagtg ccgatgaaat ttttagaaga ttgtgtactg    300
atcatcctga caagcaatta aacaatgtaa aatggaaaga agttttttatt aatcgttttg    360 gtcagatgat gctagatact cctaatccga gaaagattgt agaaaaaatt attaatgaag    420
ggcttgaaaa acaaggcctg aaaaatatag atcctgaaac tacatatttc aacatttttt    480
catcttctga cagctccgat gggaacgttt ttcattataa ctctttatca gaatcctatc    540
gagttactga tgcctgccta atgaatattt ttgtggagcg ttattttgat gattgggact    600
tgctaaatag cttagccagt aatggaatat attcagtagg aaaagaagga gcttattatc    660
ctgatcatga ttatggtcca gaatataacc ctgtttgggg accaaacgaa caaatttacc    720
attctagagt gattgcagat atcctttatg ctcgctccgt atgggatgaa tttaaaaaat    780
acttcatgga gtattggcaa aaatatgctc agctttatac cgaaatgtta tctgatacat    840
ttcttgcaat ggctattcag caatatacac gacaaacgct tactgatgaa ggcttttctta    900 tggtttgtaa cacatattat ggcaataagg aagaagttca aataactcta ctagatatct    960
atggataccc ttccactgat ataatttgta tagagcaaaa agggcttcct actcctaaag    1020 tgatactttta cattcctgga ggaacacaac catttgttga atttcttaat acagatgatc    1080
tgaaacaatg gattgcatgg catttaaaag ataacaaaca tatggtccga ttccgcaaac    1140
atttctcgct aaaacaacgt caggaaggag aaacgtttac aggtatagat aaagcacttc    1200
aatatattgc agaagagtcc cctgaatggc ctgccaataa atacatcctt tataatccga    1260
cacatttaga aacagaaaat ttatttaaca tcatgatgaa gcgaacagaa cagcggatgc    1320
ttgaagatag tgatgtacag attagatcaa attcagaagc tacccgtgac tatgctcttt    1380
cattactcga aacctttatt tcacagttat ctgcaataga tatgttagta ccagcagtag    1440
gtatcccaat taattttgcc ctatcagcta cagcattagg acttagctcg gatattgtag    1500
ttaatggaga ttcatatgaa aagagaaaat atggaattgg gtccttagtg caatctgcat    1560
tattcacagg aattaatctt attccagtta tttcggaaac cgcagaaatt ttatcttctt    1620
tctctagaac agaagaagat attccagctt ttttttcactga agaacaagct ttagctcaac    1680
gctttgaaat agtagaagaa gaattacatt ctatctcacc tgatgatcct cctcgagaaa    1740
ttactgacga aaaatttacat aaaaattcgtc tggtacgtct taacaatgaa aatcaacctt    1800
tagttgtgtt acgaagatta ggaggaaata aatttatcag aatcgagcct ataacattcc    1860
aggaaataaa aggttctttta gtaagtgaag ttataaatcc agtgactaat aaaacgtact    1920
acgtaagcaa tgctaaacta ttaggggggct ctccttatag tccttttccgt attggattag    1980 aaggtgttttg gacaccagag gtattaaaag caagagcttc cgttattgga aagcctattg    2040
gagaatcata taaagaata ttagccaaac tacaaagaat acataacagt aatatcttag    2100
atgagcgaca aggtttaatg catgaactca tggagccttat tgatctttat gaagaatcgc    2160
aaccttcttc agagcgtttg aatgcttttttc gtgaactgcg tactcaatta gaaaaagcgc    2220
tttatcttcc tgaaatggaa gcattaaaaa aacaaatact acagattcct aacaaaggtt    2280
ctggtgccgc tcgatttttta cttcgtacag ccatgaatga aatggctgga aaaaccagtg    2340
aaagcacggc tgatttaata cgctttgcct tgcaagatac agtaatttca gcgcctttttc    2400 gcggatatgc tggtgcgatt ccagaggcaa tagactttcc tgtaaaatat gtaatagaag    2460
```

-continued

```
acatatctgt atttgataaa atacagacaa attactggga acttcctgct tatgaaagct    2520
ggaacgaagg aagtaatagc cgattactgc ctggtttgtt acgtgaatcg caaagcaagg    2580
ggatgttaag taagtgtcgt atcatagaaa atagcctttta tattggacat agctatgaag   2640
aaatgtttta cagcatttct ccatattcaa accaggttgg agggccttat gaattatatc    2700 cttcacttt tttcagtatg cttcaagaag tacaaggtga tttaggattt gagcaggcct     2760
ttgccacacg taacttttc aatactcttg tttctgatcg actatcctta atggaaaata    2820
cgatgttact tacagaaagt tttgattata caccttggga tgctatttat ggagatatta    2880
attatgatga acaatttgct gcaatgtcta ttaatgaacg catagaaaaa tgtatgaata    2940
cctatagagg tgtggcattc caaaactctt caaaaagtat tgacttttc ctaataatc     3000 taaccacatt cattgataat ggactaaccg aaattgctat atctgattta ccgtatgata    3060
ttgtgcaaca agaaatctct caattcttac aaggaagtaa tgaatggaaa acacttgatg    3120
ccatgttatt taacttagat aaaggagata ttaatggtgc tttcagaaag cttctgcaat    3180
cagcaaaaga taataatata aaatttagag ctagggca ttcagataat tctgttccgc      3240
catttaataa cccttataag tctttatatt ataaggaaa tataatagct gaagcaattg    3300
aaaaactaga tcgagaaggt caaaaatttg ttgtatttgc tgatagttct ctgctcaaca    3360
gcacgcctgg gacaggtcgt cctatgccag gactagttca atatttaaaa ataccagcaa    3420
ctgtagtaga tagcgatggt gcatggcaat ttcttccaga tgtagcttca agcagagttc    3480
ctattgaagt tacagagtta gaaaattggc aagtcttaac tcctccacaa ggtaagattc    3540
ttggattaaa gcaatttaag ttaacggcag ttttccaac agaacaaagt cgcttacctc    3600
ttttagagaa ttcggtttct gaagatttaa gggaagaatt aatgcaaaag attgatgcaa    3660
taaaaaatga tgtgaaaatg aatagtttag tgtgtatgga agctggctct tgtgattcag    3720
taagccctaa ggtagctgcc cgtcttaaag atatggggtt agaagctggg atgggtgctt    3780
ctattacctg gtggagacgt gaaggcggga tggaatttc acatcagatg catactactg     3840
cttcctttaa atttgctggt aaagagtttg ccgtggatgc ttcacattta caatttgtac    3900
acgaccaatt agatacaact atcctgatac tacctgtaga tgattgggct ttagaaatag    3960
ctcaaagaaa tcgggctatt aatccttttg tggaatatgt tagtaaaaca ggaaacatgt    4020
tagcactctt catgcctcct cttttcacaa agcctcgctt aacaagagca ctataactaa    4080
ttaaaaactg tattaaagcc ttatattata aggctttaat tttctttcaa gaattattaa    4140
gtagaagaat caaaatcaat gagatagata aaatcaaatg ttattaccaa tacaactttc    4200
ttaagtatac tttttgaatt ttttgcgtta ataaatttat aatacccta actcaataaa     4260 agaagttatt gagaagttta aatcttgtga gcaagatgaa gatataattt cagcaatcga    4320
tcttattagc gcttcatata gaagggctgt ggatgcagtg gaacaa agattcggtt ctag    4380
```

<210> SEQ ID NO 2
<211> LENGTH: 1285
<212> TYPE: PRT
<213> ORGANISM: Pasteurella multocida

<400> SEQUENCE: 2

Met Lys Thr Lys His Phe Phe Asn Ser Asp Phe Thr Val Lys Gly Lys
1 5 10 15

Ser Ala Asp Glu Ile Phe Arg Arg Leu Cys Thr Asp His Pro Asp Lys
20 25 30

Gln Leu Asn Asn Val Lys Trp Lys Glu Val Phe Ile Asn Arg Phe Gly

```
            35                  40                  45
Gln Met Met Leu Asp Thr Pro Asn Pro Arg Lys Ile Val Glu Lys Ile
 50                  55                  60

Ile Asn Glu Gly Leu Glu Lys Gln Gly Leu Lys Asn Ile Asp Pro Glu
 65                  70                  75                  80

Thr Thr Tyr Phe Asn Ile Phe Ser Ser Asp Ser Ser Asp Gly Asn
                 85                  90                  95

Val Phe His Tyr Asn Ser Leu Ser Glu Ser Tyr Arg Val Thr Asp Ala
                100                 105                 110

Cys Leu Met Asn Ile Phe Val Glu Arg Tyr Phe Asp Asp Trp Asp Leu
                115                 120                 125

Leu Asn Ser Leu Ala Ser Asn Gly Ile Tyr Ser Val Gly Lys Glu Gly
        130                 135                 140

Ala Tyr Tyr Pro Asp His Asp Tyr Gly Pro Glu Tyr Asn Pro Val Trp
145                 150                 155                 160

Gly Pro Asn Glu Gln Ile Tyr His Ser Arg Val Ile Ala Asp Ile Leu
                165                 170                 175

Tyr Ala Arg Ser Val Trp Asp Glu Phe Lys Lys Tyr Phe Met Glu Tyr
                180                 185                 190

Trp Gln Lys Tyr Ala Gln Leu Tyr Thr Glu Met Leu Ser Asp Thr Phe
        195                 200                 205

Leu Ala Met Ala Ile Gln Gln Tyr Thr Arg Gln Thr Leu Thr Asp Glu
        210                 215                 220

Gly Phe Leu Met Val Cys Asn Thr Tyr Gly Asn Lys Glu Glu Val
225                 230                 235                 240

Gln Ile Thr Leu Leu Asp Ile Tyr Gly Tyr Pro Ser Thr Asp Ile Ile
                245                 250                 255

Cys Ile Glu Gln Lys Gly Leu Pro Thr Pro Lys Val Ile Leu Tyr Ile
                260                 265                 270

Pro Gly Gly Thr Gln Pro Phe Val Glu Phe Leu Asn Thr Asp Asp Leu
        275                 280                 285

Lys Gln Trp Ile Ala Trp His Leu Lys Asp Asn Lys His Met Val Arg
290                 295                 300

Phe Arg Lys His Phe Ser Leu Lys Gln Arg Gln Glu Gly Glu Thr Phe
305                 310                 315                 320

Thr Gly Ile Asp Lys Ala Leu Gln Tyr Ile Ala Glu Glu Ser Pro Glu
                325                 330                 335

Trp Pro Ala Asn Lys Tyr Ile Leu Tyr Asn Pro Thr His Leu Glu Thr
                340                 345                 350

Glu Asn Leu Phe Asn Ile Met Met Lys Arg Thr Glu Gln Arg Met Leu
        355                 360                 365

Glu Asp Ser Asp Val Gln Ile Arg Ser Asn Ser Glu Ala Thr Arg Asp
        370                 375                 380

Tyr Ala Leu Ser Leu Leu Glu Thr Phe Ile Ser Gln Leu Ser Ala Ile
385                 390                 395                 400

Asp Met Leu Val Pro Ala Val Gly Ile Pro Ile Asn Phe Ala Leu Ser
                405                 410                 415

Ala Thr Ala Leu Gly Leu Ser Ser Asp Ile Val Val Asn Gly Asp Ser
                420                 425                 430

Tyr Glu Lys Arg Lys Tyr Gly Ile Gly Ser Leu Val Gln Ser Ala Leu
        435                 440                 445

Phe Thr Gly Ile Asn Leu Ile Pro Val Ile Ser Glu Thr Ala Glu Ile
450                 455                 460
```

```
Leu Ser Ser Phe Ser Arg Thr Glu Glu Asp Ile Pro Ala Phe Phe Thr
465                 470                 475                 480

Glu Glu Gln Ala Leu Ala Gln Arg Phe Glu Ile Val Glu Glu Glu Leu
                485                 490                 495

His Ser Ile Ser Pro Asp Asp Pro Arg Glu Ile Thr Asp Glu Asn
            500                 505                 510

Leu His Lys Ile Arg Leu Val Arg Leu Asn Asn Glu Asn Gln Pro Leu
                515                 520                 525

Val Val Leu Arg Arg Leu Gly Gly Asn Lys Phe Ile Arg Ile Glu Pro
530                 535                 540

Ile Thr Phe Gln Glu Ile Lys Gly Ser Leu Val Ser Glu Val Ile Asn
545                 550                 555                 560

Pro Val Thr Asn Lys Thr Tyr Tyr Val Ser Asn Ala Lys Leu Leu Gly
                565                 570                 575

Gly Ser Pro Tyr Ser Pro Phe Arg Ile Gly Leu Glu Gly Val Trp Thr
                580                 585                 590

Pro Glu Val Leu Lys Ala Arg Ala Ser Val Ile Gly Lys Pro Ile Gly
                595                 600                 605

Glu Ser Tyr Lys Arg Ile Leu Ala Lys Leu Gln Arg Ile His Asn Ser
610                 615                 620

Asn Ile Leu Asp Glu Arg Gln Gly Leu Met His Glu Leu Met Glu Leu
625                 630                 635                 640

Ile Asp Leu Tyr Glu Glu Ser Gln Pro Ser Ser Glu Arg Leu Asn Ala
                645                 650                 655

Phe Arg Glu Leu Arg Thr Gln Leu Glu Lys Ala Leu Tyr Leu Pro Glu
                660                 665                 670

Met Glu Ala Leu Lys Lys Gln Ile Leu Gln Ile Pro Asn Lys Gly Ser
                675                 680                 685

Gly Ala Ala Arg Phe Leu Leu Arg Thr Ala Met Asn Glu Met Ala Gly
                690                 695                 700

Lys Thr Ser Glu Ser Thr Ala Asp Leu Ile Arg Phe Ala Leu Gln Asp
705                 710                 715                 720

Thr Val Ile Ser Ala Pro Phe Arg Gly Tyr Ala Gly Ala Ile Pro Glu
                725                 730                 735

Ala Ile Asp Phe Pro Val Lys Tyr Val Ile Glu Asp Ile Ser Val Phe
                740                 745                 750

Asp Lys Ile Gln Thr Asn Tyr Trp Glu Leu Pro Ala Tyr Glu Ser Trp
                755                 760                 765

Asn Glu Gly Ser Asn Ser Arg Leu Leu Pro Gly Leu Leu Arg Glu Ser
                770                 775                 780

Gln Ser Lys Gly Met Leu Ser Lys Cys Arg Ile Ile Glu Asn Ser Leu
785                 790                 795                 800

Tyr Ile Gly His Ser Tyr Glu Glu Met Phe Tyr Ser Ile Ser Pro Tyr
                805                 810                 815

Ser Asn Gln Val Gly Gly Pro Tyr Glu Leu Tyr Pro Phe Thr Phe Phe
                820                 825                 830

Ser Met Leu Gln Glu Val Gln Gly Asp Leu Gly Phe Gly Gln Ala Phe
                835                 840                 845

Ala Thr Arg Asn Phe Phe Asn Thr Leu Val Ser Asp Arg Leu Ser Leu
                850                 855                 860

Met Glu Asn Thr Met Leu Leu Thr Glu Ser Phe Asp Tyr Thr Pro Trp
865                 870                 875                 880

Asp Ala Ile Tyr Gly Asp Ile Asn Tyr Asp Glu Gln Phe Ala Ala Met
                885                 890                 895
```

-continued

```
Ser Ile Asn Glu Arg Ile Glu Lys Cys Met Asn Thr Tyr Arg Gly Val
            900                 905                 910
Ala Phe Gln Asn Ser Ser Lys Ser Ile Asp Phe Phe Leu Asn Asn Leu
            915                 920                 925
Thr Thr Phe Ile Asp Asn Gly Leu Thr Glu Ile Ala Ile Ser Asp Leu
            930                 935                 940
Pro Tyr Asp Ile Val Gln Gln Glu Ile Ser Gln Phe Leu Gln Gly Ser
945                 950                 955                 960
Asn Glu Trp Lys Thr Leu Asp Ala Met Leu Phe Asn Leu Asp Lys Gly
                965                 970                 975
Asp Ile Asn Gly Ala Phe Arg Lys Leu Leu Gln Ser Ala Lys Asp Asn
            980                 985                 990
Asn Ile Lys Phe Arg Ala Ile Gly His Ser Asp Asn Ser Val Pro Pro
            995                 1000                1005
Phe Asn Asn Pro Tyr Lys Ser Leu Tyr Tyr Lys Gly Asn Ile Ile
    1010                1015                1020
Ala Glu Ala Ile Glu Lys Leu Asp Arg Glu Gly Gln Lys Phe Val
    1025                1030                1035
Val Phe Ala Asp Ser Ser Leu Leu Asn Ser Thr Pro Gly Thr Gly
    1040                1045                1050
Arg Pro Met Pro Gly Leu Val Gln Tyr Leu Lys Ile Pro Ala Thr
    1055                1060                1065
Val Val Asp Ser Asp Gly Ala Trp Gln Phe Leu Pro Asp Val Ala
    1070                1075                1080
Ser Ser Arg Val Pro Ile Glu Val Thr Glu Leu Glu Asn Trp Gln
    1085                1090                1095
Val Leu Thr Pro Pro Gln Gly Lys Ile Leu Gly Leu Lys Gln Phe
    1100                1105                1110
Lys Leu Thr Ala Gly Phe Pro Thr Glu Gln Ser Arg Leu Pro Leu
    1115                1120                1125
Leu Glu Asn Ser Val Ser Glu Asp Leu Arg Glu Glu Leu Met Gln
    1130                1135                1140
Lys Ile Asp Ala Ile Lys Asn Asp Val Lys Met Asn Ser Leu Val
    1145                1150                1155
Cys Met Glu Ala Gly Ser Cys Asp Ser Val Ser Pro Lys Val Ala
    1160                1165                1170
Ala Arg Leu Lys Asp Met Gly Leu Glu Ala Gly Met Gly Ala Ser
    1175                1180                1185
Ile Thr Trp Trp Arg Arg Glu Gly Gly Met Glu Phe Ser His Gln
    1190                1195                1200
Met His Thr Thr Ala Ser Phe Lys Phe Ala Gly Lys Glu Phe Ala
    1205                1210                1215
Val Asp Ala Ser His Leu Gln Phe Val His Asp Gln Leu Asp Thr
    1220                1225                1230
Thr Ile Leu Ile Leu Pro Val Asp Asp Trp Ala Leu Glu Ile Ala
    1235                1240                1245
Gln Arg Asn Arg Ala Ile Asn Pro Phe Val Glu Tyr Val Ser Lys
    1250                1255                1260
Thr Gly Asn Met Leu Ala Leu Phe Met Pro Pro Leu Phe Thr Lys
    1265                1270                1275
Pro Arg Leu Thr Arg Ala Leu
    1280                1285
```

<210> SEQ ID NO 3
<211> LENGTH: 31
<212> TYPE: DNA
<213> ORGANISM: Artificial sequence
<220> FEATURE:
<223> OTHER INFORMATION: PMT-specific forward primer

<400> SEQUENCE: 3
agaggttatg gatccgaaaa caaaacattt t                          31

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
atagtagaag aagaattaca                                       20

<210> SEQ ID NO 5
<211> LENGTH: 34
<212> TYPE: DNA
<213> ORGANISM: Artificial sequence
<220> FEATURE:
<223> OTHER INFORMATION: Primer

<400> SEQUENCE: 5
ctaacataga ggccatggat atgaaaacaa aaca                       34

<210> SEQ ID NO 6
<211> LENGTH: 34
<212> TYPE: DNA
<213> ORGANISM: Artificial sequence
<220> FEATURE:
<223> OTHER INFORMATION: Primer

<400> SEQUENCE: 6
acttcgtaca gccatgaatg aaatggctgg aaaa                       34

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
actcaattag aaaaagcgct                                       20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
ctactacagt tgctggtatt                                       20

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9

```
attgttaaga cgtaccagac ga                                              22

<210> SEQ ID NO 10
<211> LENGTH: 33
<212> TYPE: DNA
<213> ORGANISM: Artificial sequence
<220> FEATURE:
<223> OTHER INFORMATION: Primer

<400> SEQUENCE: 10
ctcttgttaa gctagccttt gtgaaaagag gag                                  33

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11 ttcttcccctt aaatcttcag                                                20

<210> SEQ ID NO 12
<211> LENGTH: 32
<212> TYPE: DNA
<213> ORGANISM: Artificial sequence
<220> FEATURE:
<223> OTHER INFORMATION: Primer

<400> SEQUENCE: 12
tcactggttt ttccagccat ttcattcatg gc                                   32

<210> SEQ ID NO 13
<211> LENGTH: 10
<212> TYPE: DNA
<213> ORGANISM: Artificial sequence
<220> FEATURE:
<223> OTHER INFORMATION: Synthetic random primer

<400> SEQUENCE: 13
aagcggcctc                                                            10
```